United States Patent
Malone et al.

(10) Patent No.: US 9,321,721 B2
(45) Date of Patent: Apr. 26, 2016

(54) KINASE INHIBITORS

(71) Applicant: Allergan, Inc., Irvine, CA (US)

(72) Inventors: Thomas C. Malone, Irvine, CA (US); C. Eugene Hull, III, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/198,964

(22) Filed: Mar. 6, 2014

(65) Prior Publication Data

US 2014/0256819 A1   Sep. 11, 2014

Related U.S. Application Data

(60) Provisional application No. 61/774,822, filed on Mar. 8, 2013.

(51) Int. Cl.
| | | |
|---|---|---|
| A61K 31/17 | (2006.01) | |
| A01N 47/28 | (2006.01) | |
| C07C 273/00 | (2006.01) | |
| C07C 275/00 | (2006.01) | |
| C07C 275/40 | (2006.01) | |
| C07C 275/30 | (2006.01) | |

(52) U.S. Cl.
CPC ............. *C07C 275/40* (2013.01); *C07C 275/30* (2013.01)

(58) Field of Classification Search
None
See application file for complete search history.

(56) References Cited

FOREIGN PATENT DOCUMENTS

| EP | 2060565 | 5/2009 | | |
|---|---|---|---|---|
| EP | 2070928 | 6/2009 | | |
| JP | WO 0121577 A2 * | 3/2001 | ............ | C07C 217/74 |
| WO | 0121577 | 3/2001 | | |
| WO | WO 0121577 A2 * | 3/2001 | | |
| WO | 2005030705 | 4/2005 | | |
| WO | 2009098458 | 8/2009 | | |
| WO | 2010092440 | 8/2010 | | |

OTHER PUBLICATIONS

Adamis, A., et al., Inhibition of Platelet-Derived Growth Factor B Signaling Enhances the Efficacy of Anti-Vascular Endothelial Growth Factor Therapy in Multiple Models of Ocular Neovascularization, Amer. Journal Pathology 2006, 168: 2036-2053, 6.

Aora, A., et al., Role of Tyrosine Kinase Inhibitors in Cancer Therapy, J. Pharma. & Exp. Therapeutics 2015, 315: 971-979, 3.

Baraket, M., et al., VEGF inhibitors for the treatment of neovascular age-related macular degeneration, Informa Healthcare, 2009, 637-646.

Bergers, G., et al., Benefits of targeting both pericytes and endothelial cells in the tumor vasculature with kinase inhibitors, J. Clin. Invest. 2003, 111: 1287-1295, 9.

Chappelow, A., et al., Neovascular Age-Related Macular Degeneration Potential Therapies, Drugs 2008, 68: 1029-1036, 8.

Cowan-Jacob, S.W., Structural biology of protein tyrosine kinases, Cell. Mol. Life Sci. 2006, 63: 2608-2625.

Notification of Transmittal of the International Search Report and Written Opinion mailed on May 28, 2014 for PCT/US2014/021345 filed on Mar. 6, 2014 in the name of Allergan, Inc.

DePinho, R., et al., Coactivation of Receptor Tyrosine Kinases Affects the Response of Tumor Cells to Targeted Therapies, Science 2007, 318: 287-291.

Heidenreich, R., et al., Angiogenesis: The New Potential Target for the Therapy of Psoriasis?, Drug News Perspect 2008, 21:97-105, 2.

Ni, Z., et al., Emerging Pharmacologic Therapies for Wet Age-Related Macular Degeneration, Ophthalmologica 2009, 223: 401-410.

Smith, J., et al., Expression of vascular endothelial growth factor and its receptors in rosacea, Br. J. Ophthalmol. 2007, 91: 226-229.

Zhang, X., et al., Vascular endothelial growth factor-A: A multifunctional molecular player in diabetic retinopathy, Int'l. J. Biochem. & Cell Biol. 2009, 41: 2368-2371.

* cited by examiner

*Primary Examiner* — Jeffrey S Lundgren
*Assistant Examiner* — Tori M Strong
(74) *Attorney, Agent, or Firm* — Jonathan Bass

(57) ABSTRACT

The present invention relates to compounds of formula I

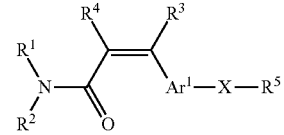

or a pharmaceutically acceptable salts thereof; wherein the variables $R^1$—$R^5$, $Ar^1$, and X are as defined herein. The compounds are capable of modulating tyrosine kinase signal transduction in order to regulate, modulate and/or inhibit abnormal cell proliferation.

15 Claims, No Drawings

KINASE INHIBITORS

This application claims the benefit of U.S. Provisional Application Ser. No. 61/774,822 filed on Mar. 8, 2013, which is incorporated by reference herein in its entirety.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The receptor-type tyrosine kinases (RTKs) comprise a large family of transmembrane receptors with diverse biological activities. The intrinsic function of RTKs is activated upon ligand binding, which results in phosphorylation of the receptor and multiple cellular substrates, and subsequently in a variety of cellular responses. The non-receptor tyrosine kinases represent a collection of cellular enzymes which lack extracellular and transmembrane sequences. A more detailed discussion of receptor and non-receptor tyrosine kinases is provided in Cowan-Jacob Cell Mol. Life Sci., 2996, 63, 2608-2625 which is incorporated herein by reference.

There are a number of examples where RTK kinases, have been found to be involved in cellular signaling pathways leading to pathological conditions, including exudative age-related macular degeneration (Ni et al. Opthalmologica 2009 223 401-410; Chappelow et al. Drugs 2008 68 1029-1036), diabetic retinopathy (Zhang et al., Int. J. Biochem. Cell Biol. 2009 41 2368-2371), cancer (Aora et al. J. Path. Exp. Ther. 2006, 315, 971), psoriasis (Heidenreich et al Drug News Perspective 2008 21 97-105), rosacea (Smith, J. R., V. B. Lanier, et al. Br J Ophthalmol 2007, 91(2): 226-229) and hyper immune response. In ophthalmic diseases such as exudative age-related macular degeneration and diabetic retinopathy aberrant activation of VEGF receptors can lead to abnormal blood vessel growth. The importance of VEGFR signaling in the exudative age-related macular degeneration disease process is evident by the clinical success of multiple anti-VEGF targeting agents including Lucentis®, Avastin®, and EYLEA™ (Barakat et al., Expert Opin. Investig. Drugs 2009, 18, 637). Recently it has been suggested that inhibition of multiple RTK signaling pathways may provide a greater therapeutic effect than targeting a single RTK signaling pathway. For example in neovascular ocular disorders such as exudative age-related macular degeneration and diabetic retinopathy the inhibition of both VEGFR and PDGFRβ may provide a greater therapeutic effect in by causing regression of existing neovascular blood vessels present in the disease (Adamis et al., Am. J. Pathol. 2006 168 2036-2053). In cancer inhibition of multiple RTK signaling pathways has been suggested to have a greater effect than inhibiting a single RTK pathway (DePinho et al., Science 2007 318 287-290; Bergers et al. J. Clin Invest. 2003 111 1287-1295).

The identification of effective small compounds which specifically inhibit signal transduction by modulating the activity of receptor and non-receptor tyrosine kinases to regulate and modulate abnormal or inappropriate cell proliferation is therefore desirable and one object of this invention.

The above references are hereby incorporated by reference in their entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction by blocking the VEGF and/or PDGF receptors. Such compounds are useful for the treatment of diseases related to unregulated tyrosine kinase signal transduction, including vascular proliferative disorders such as diabetic retinopathy, age-related macular degeneration and retinopathy of prematurity.

In one illustrative embodiment, the compounds of the present invention have the following general formula I:

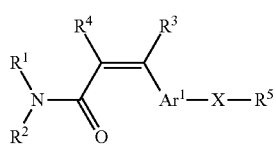

wherein:
$R^1$ is selected from the group consisting of hydrogen and lower alkyl;
$R^2$ is selected from the group consisting of hydrogen and lower alkyl;
$R^3$ is selected from the group consisting of hydrogen, alkyl, e.g. lower alkyl, aryl and substituted aryl, e.g. carbocyclic aryl and substituted carbocyclic aryl;
$R^4$ is selected from the group consisting of hydrogen, $C_1$ to $C_8$ alkyl, $(CR^6R^7)_pNR^8R^9$, $(CR^6R^7)_pC(O)OR^8$ and $(CR^6R^7)_pOR^8$
$Ar^1$ is aryl, e.g. carbocyclic aryl or heteroaryl;
X is

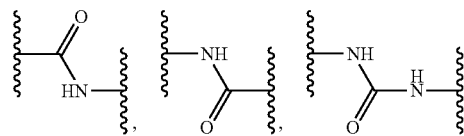

$R^5$ is aryl, e.g. carbocyclic aryl or heteroaryl, wherein said carbocyclic aryl or heteroaryl may be optionally substituted with lower alkyl, halogen, or trifluoromethyl;
$R^6$ is selected from the group consisting of hydrogen, lower alkyl, halogen, trifluoromethyl and hydroxyl;
$R^7$ selected from the group consisting of hydrogen. lower alkyl halogen, trifluoromethyl and hydroxyl;
$R^8$ is selected from the group consisting of hydrogen and lower alkyl
$R^9$ is selected from the group consisting of hydrogen and lower alkyl, or
$R^8$ and $R^9$ may be taken together with N to form a heterocyclic ring;
p is an integer of from 1 to 6; and
prodrugs, pharmaceutically acceptable salts, racemic mixtures and enantiomers of said compound.

In one embodiment, $R^1$ is hydrogen.
In another embodiment, $R^2$ is hydrogen.
In another embodiment, $R^3$ is selected from the group consisting of hydrogen, phenyl and alkyloxyphenyl, e.g. methoxyphenyl.
In another embodiment, $R^4$ is hydrogen;
In another embodiment, $Ar^1$ is phenyl.
In another embodiment, X is —HN—C(O)—NH—.
In another embodiment, $R^5$ is selected from the group consisting of phenyl and halo-substituted and halo lower alkyl-substituted phenyl, e.g. fluorophenyl, trifluoromethylphenyl and fluoro, trifluoromethylphenyl.
In another embodiment, $R^5$ is a fluoro, trifluoromethylphenyl, e.g. 2-fluoro-5-trifluoromethylphenyl.

In another embodiment, said compound has an $IC_{50}$ value for compound inhibition in the VEGFR2 Kinase Assay of less than 1000 nM.

Compounds of formula I are useful as kinase inhibitors. As such, compounds of formula I will be useful for treating diseases related to unregulated tyrosine kinase signal transduction, for example, cancer, blood vessel proliferative disorders, fibrotic disorders, and neurodegenerative diseases. In particular, the compounds of the present invention are useful for treatment of mesangial cell proliferative disorders and metabolic diseases, pterigium, arthritis, restenosis, hepatic cirrhosis, atherosclerosis, psoriasis, rosacea, diabetes mellitus, wound healing, inflammation and neurodegenerative diseases and preferably ophthalmic diseases, i.e. diabetic retinopathy, age-related macular degeneration, retinopathy of prematurity, etc.

DETAILED DESCRIPTION OF THE INVENTION

The present invention is further directed to pharmaceutical compositions comprising a pharmaceutically effective amount of one or more of the above described compounds and a pharmaceutically acceptable carrier or excipient, wherein said compositions are effective for treating the above diseases and conditions; especially ophthalmic diseases and conditions. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, rosacea, atherosclerosis, arthritis, and other disorders related to abnormal vasculogenesis and/or angiogenesis, such as exudative age related macular degeneration and diabetic retinopathy The following defined terms are used throughout this specification:
"EtOAc" refers to ethyl acetate
"PDGFRβ" refers to platelet-derived growth factor beta
"PTK" refers to protein tryrosine kinase
"rt" refers to room temperature
"RTK" refers to receptor tyrosine kinase
"VEGFR" refers to vascular endothelial growth factor receptor
"VEGF" refers to vascular endothelial growth factor
"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halo, nitrogen, oxygen, sulfur or phosphorus atom, e.g. fluoro, chloro, cyano, nitro, dialkylamino, hydroxyl, phosphate, thiol, etc.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also refer to those salts which retain the biological effectiveness and properties of the free acid and which are obtained by reaction with inorganic bases such as sodium hydroxide, calcium hydroxide, magnesium hydroxide, zinc hydroxide or by organic bases such as tromethamine, choline, diethylamine and lysine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, NO$_2$, halogen, dimethyl amino, and SH.

"Alkoxy" refers to O-alkyl.

"Alkoxycarbonyl" refers to —C(O)O-alkyl or —C(O)O-aryl.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, NO$_2$, amine, thioether, cyano, alkoxy, alkyl, and amino "Carbocyclic aryl" refers to an aryl group wherein the ring atoms are carbon.

"Heteroaryl" or "heterocyclic aryl" refers to an aryl group having from 1 to 3 heteroatoms as ring atoms, the remainder of the ring atoms being carbon. Heteroatoms include oxygen, sulfur, and nitrogen. Thus, heteroaryl groups include furanyl, thienyl, pyridyl, pyrrolyl, N-lower alkyl pyrrolo, pyrimidyl, pyrazinyl, imidazolyl and the like.

The compounds of this invention may be prepared by the general reaction schemes set forth below.

Scheme 1

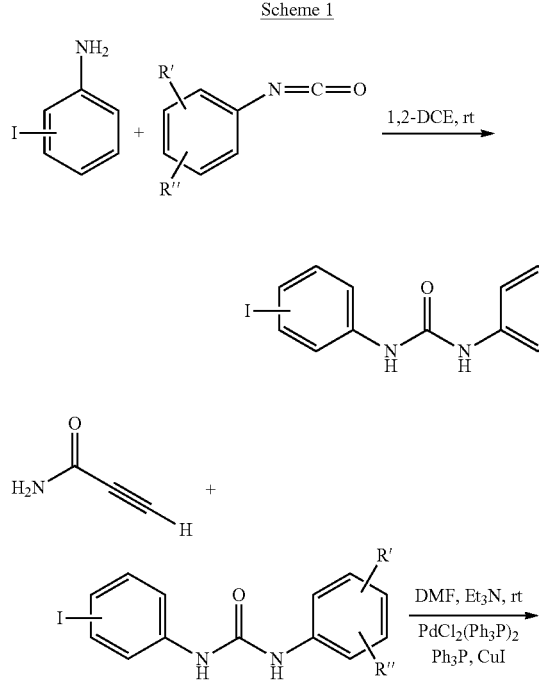

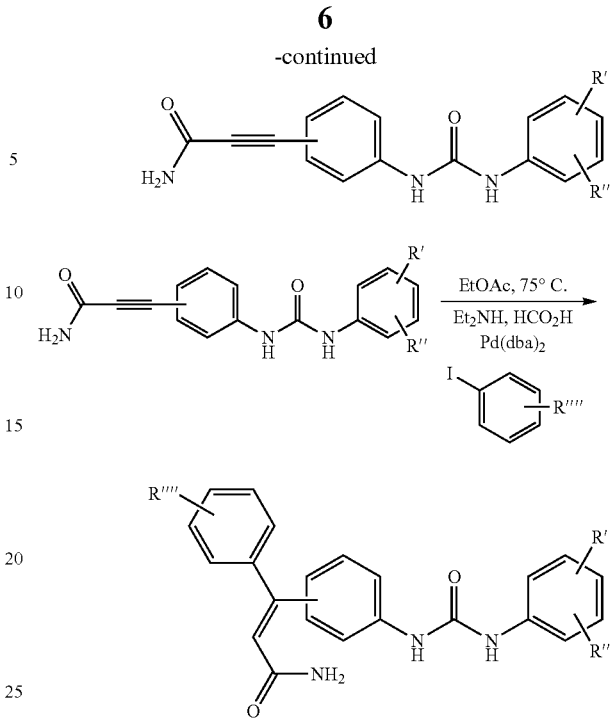

Scheme 2

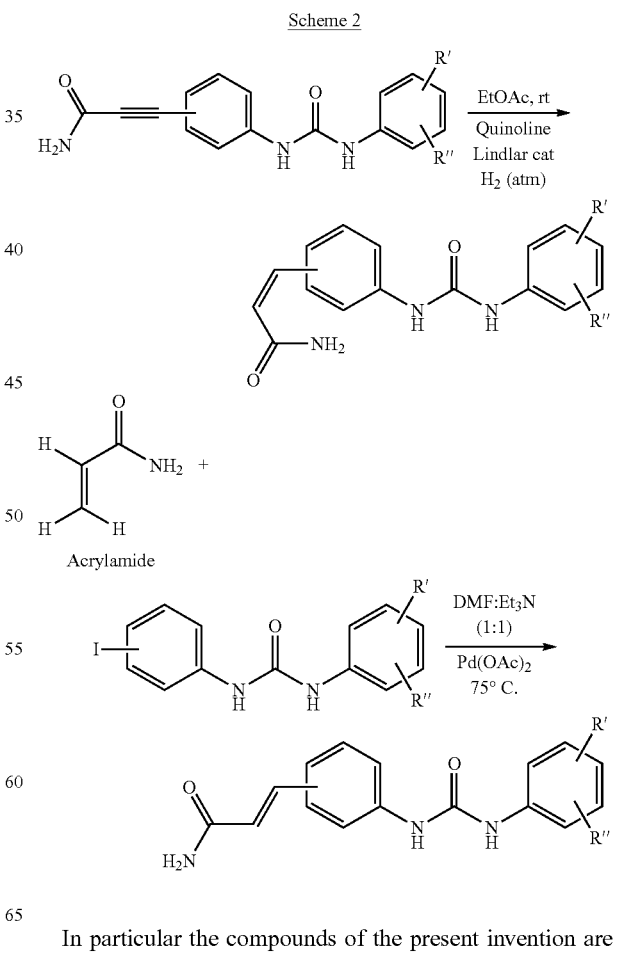

In particular the compounds of the present invention are selected from the compounds of Table 1, below.

TABLE 1

| Example Number | Structure | Chemical Name |
|---|---|---|
| Example 1 | 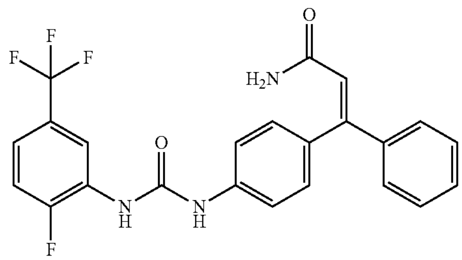 [SMILES: NC(=O)/C=C(/c1ccccc1)c1ccc(NC(=O)Nc2cc(C(F)(F)F)ccc2F)cc1] | (2Z)-3-{4-[({[2-fluoro-5-(trifluoromethyl)phenyl]amino}-carbonyl)amino]phenyl}-3-phenylacrylamide |
| Example 2 | 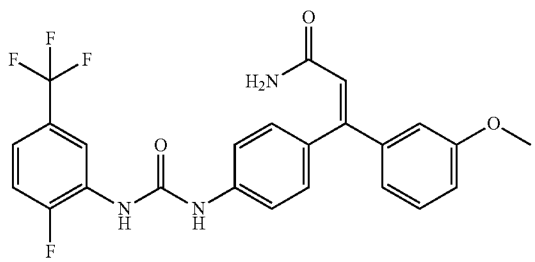 [SMILES: COc1cccc(/C(=C/C(N)=O)c2ccc(NC(=O)Nc3cc(C(F)(F)F)ccc3F)cc2)c1] | (2E)-3-{4-[({[2-fluoro-5-(trifluoromethyl)phenyl]amino}-carbonyl)amino]phenyl}-3-(3-methoxyphenyl)acrylamide |
| Example 3 | 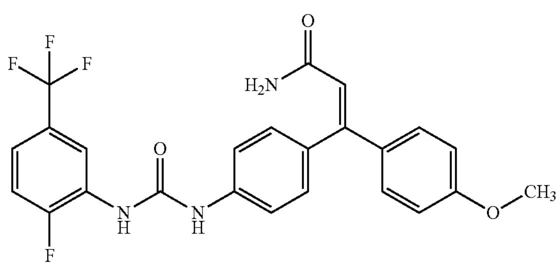 [SMILES: COc1ccc(/C(=C/C(N)=O)c2ccc(NC(=O)Nc3cc(C(F)(F)F)ccc3F)cc2)cc1] | (2E)-3-{4-[({[2-fluoro-5-(trifluoromethyl)phenyl]amino}-carbonyl)amino]phenyl}-3-(4-methoxyphenyl)acrylamide |
| Example 4 | 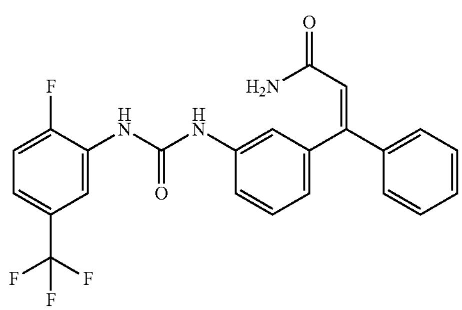 [SMILES: NC(=O)/C=C(/c1ccccc1)c1cccc(NC(=O)Nc2cc(C(F)(F)F)ccc2F)c1] | (2Z)-3-{3-[({[2-fluoro-5-(trifluoromethyl)phenyl]amino}-carbonyl)amino]phenyl}-3-phenylacrylamide |
| Example 5 | 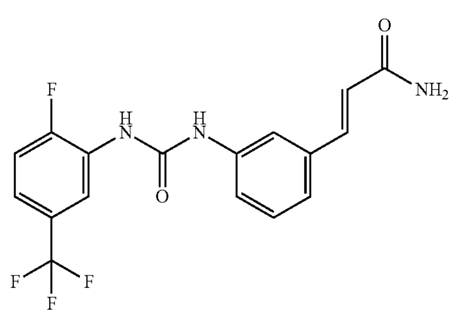 [SMILES: NC(=O)/C=C/c1cccc(NC(=O)Nc2cc(C(F)(F)F)ccc2F)c1] | (2E)-3-{3-[({[2-fluoro-5-(trifluoromethyl)phenyl]amino}-carbonyl)amino]phenyl}acrylamide |

TABLE 1-continued

| Example Number | Structure | Chemical Name |
|---|---|---|
| Example 6 | 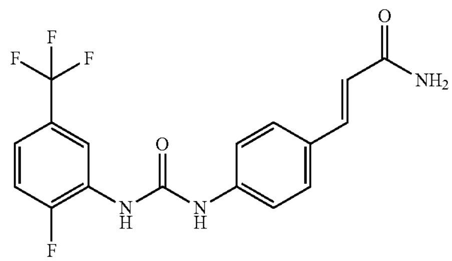 [SMILES: NC(=O)/C=C/c1ccc(NC(=O)Nc2cc(C(F)(F)F)ccc2F)cc1] | (2E)-3-{4-[({[2-fluoro-5-(trifluoromethyl)phenyl]amino}-carbonyl)amino]phenyl}acrylamide |
| Example 7 | 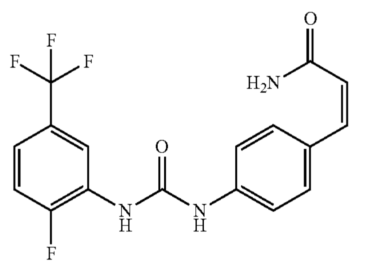 [SMILES: NC(=O)/C=C\c1ccc(NC(=O)Nc2cc(C(F)(F)F)ccc2F)cc1] | (2Z)-3-{4-[({[2-fluoro-5-(trifluoromethyl)phenyl]amino}-carbonyl)amino]phenyl}acrylamide |
| Example 8 | 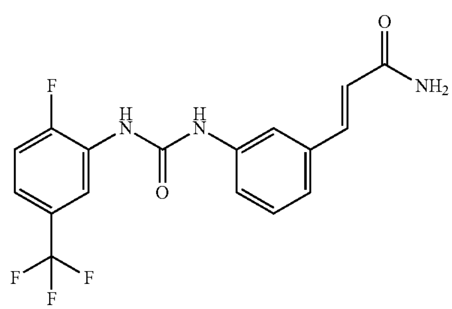 [SMILES: NC(=O)/C=C/c1cccc(NC(=O)Nc2cc(C(F)(F)F)ccc2F)c1] | (2E)-3-{3-[({[2-fluoro-5-(trifluoromethyl)phenyl]amino}-carbonyl)amino]phenyl}acrylamide |

Biological data for the compounds of the present invention was generated by use of the following assay.

VEGFR2 kinase potency of select analogs was determined by the following assay:

VEGFR2Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

TABLE 2
VEGFR2 Kinase activity for Select Analogs
| Example Number | Structure | VEGFR2 Kinase Assay (IC$_{50}$ nM) |
| --- | --- | --- |
| Example 1 | 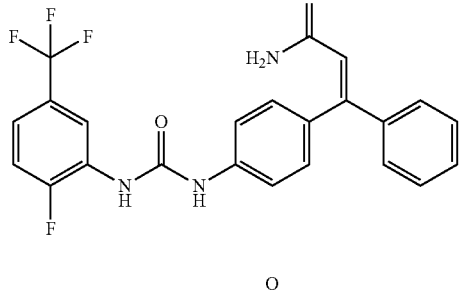 | 626 |
| Example 2 | 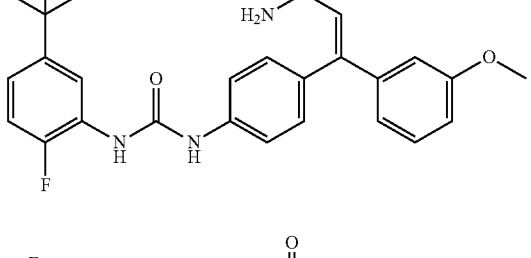 | 945 |
| Example 3 | 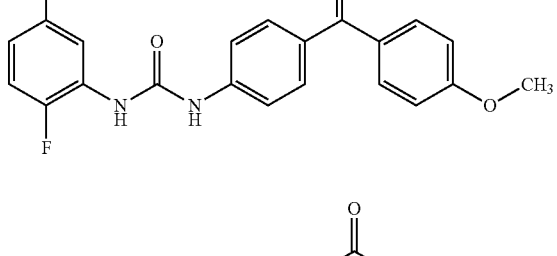 | 457 |
| Example 4 | 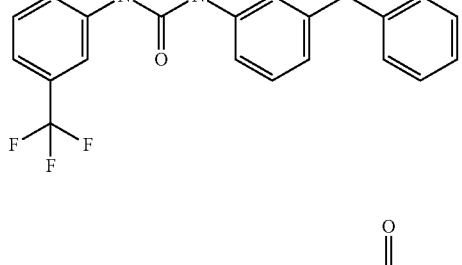 | >10000 |
| Example 5 | 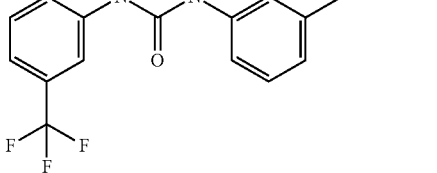 | >10000 |

TABLE 2-continued

VEGFR2 Kinase activity for Select Analogs

| Example Number | Structure | VEGFR2 Kinase Assay (IC$_{50}$ nM) |
|---|---|---|
| Example 6 | 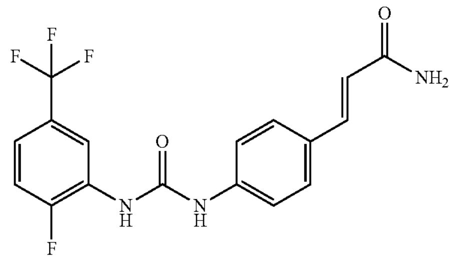 [SMILES: NC(=O)/C=C/c1ccc(NC(=O)Nc2cc(C(F)(F)F)ccc2F)cc1] | >10000 |
| Example 7 | 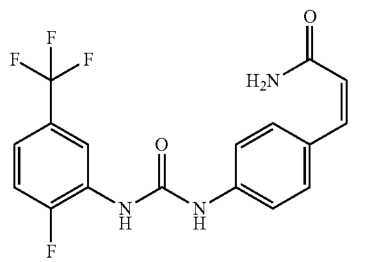 [SMILES: NC(=O)/C=C\c1ccc(NC(=O)Nc2cc(C(F)(F)F)ccc2F)cc1] | 2790 |
| Example 8 | 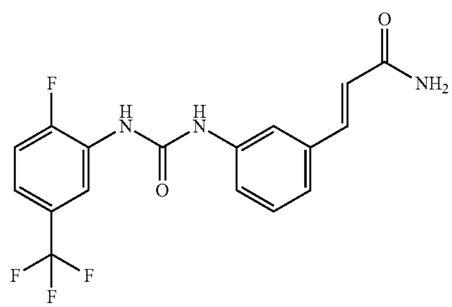 [SMILES: NC(=O)/C=C/c1cccc(NC(=O)Nc2cc(C(F)(F)F)ccc2F)c1] | >10000 |

It has been, surprisingly, found from the above data that;

The compounds of Examples 1, 2, 3, and 7 are preferred as having excellent VEGFR2 potency as shown in this assay.

The compounds of Examples 1, 2 and 3 are more preferred as having even better VEGFR2 potency as shown in this assay.

Finally, the compound of Example 3 is most preferred as having the best VEGFR2 potency as shown in this assay.

The invention is further illustrated by the following non-limiting examples.

Preparation 1

1-[2-fluoro-5-(trifluoromethyl)phenyl]-3-(4-iodophenyl)urea

To a solution of 4-iodoaniline (438 mg, 2.0 mmol) in 15.0 mL 1,2-dichloroethane at rt was added 2-fluoro-5-(trifluoromethyl)phenyl isocyanate (0.304 mL, 2.1 mmol). After 50 minutes 3 mL hexane was added, the mixture cooled to 0° C., the precipitant filtered and rinsed with 10% EtOAc/hexane to give the title compound as a light purple solid (692 mg, 82%). $^1$H NMR (DSMO-d6) δ: 9.26 (s, 1H), 8.90 (d, J=2.9 Hz, 1H), 8.59 (dd, J=7.3, 2.3 Hz, 1H), 7.60-7.65 (m, 2H), 7.46-7.54 (m, 1H), 7.36-7.43 (m, 1H), 7.29-7.34 (m, 2H).

Preparation 2

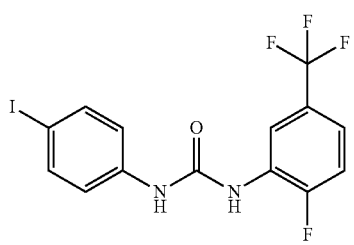 [SMILES: O=C(Nc1ccc(I)cc1)Nc1cc(C(F)(F)F)ccc1F]

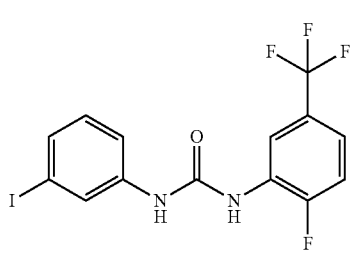 [SMILES: O=C(Nc1cccc(I)c1)Nc1cc(C(F)(F)F)ccc1F]

1-[2-fluoro-5-(trifluoromethyl)phenyl]-3-(3-iodophenyl)urea

To a solution of 3-iodoaniline (438 mg, 2.0 mmol) in 15.0 mL 1,2-dichloroethane at rt was added 2-fluoro-5-(trifluoromethyl)phenyl isocyanate (0.304 mL, 2.1 mmol). After 4 hours the precipitant was filtered and rinsed with 10% EtOAc/hexane to give the title compound as a white solid (602 mg, 71%). $^1$H NMR (DSMO-d6) δ: 9.25 (br. s, 1H), 8.91 (br. s, 1H), 8.57 (dd, J=7.3, 2.1 Hz, 1H), 8.04 (t, J=1.9 Hz, 1H), 7.46-7.54 (m, 1H), 7.42 (dd, J=4.5, 2.2 Hz, 1H), 7.35-7.40 (m, 1H), 7.28-7.33 (m, 1H), 7.06-7.14 (m, 1H)
Preparation 3

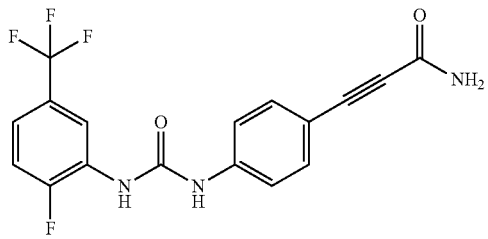 [SMILES: NC(=O)C#Cc1ccc(NC(=O)Nc2cc(C(F)(F)F)ccc2F)cc1]

3-{4-[({[2-fluoro-5-(trifluoromethyl)phenyl]amino}carbonyl)amino]phenyl}prop-2-ynamide To a mixture of propynoic acid amide (41.4 mg, 0.60 mmol), 1-[2-fluoro-5-(trifluoromethyl)phenyl]-3-(4-iodophenyl)urea (169.7 mg, 0.40 mmol), triethylamine (0.167 mL, 1.2 mmol), dichlorobis(triphenylphosphine)palladium(II) (22.5 mg, 0.032 mmol), and triphenylphosphine (5.2 mg, 0.020 mmol) in 3.0 mL DMF (degassed) was added copper (I)iodide (7.6 mg, 0.04 mmol) and the reaction stirred at rt for 17 hours. The reaction was combined with a prior test reaction (36.5 mg theoretical yield) and partitioned between EtOAc and H$_2$O/brine mixture. The EtOAc layer was washed 3 times with H$_2$O/brine mixture, then brine, dried with anhydrous Na$_2$SO$_4$ and rotary evaporated to a solid. The solid was chromatographed eluting with EtOAc/CHCl$_3$ and then triturated with EtOAc/hexane to give the title compound as a light tan solid (118.5 mg, 65%). $^1$H NMR (DSMO-d6) δ: 9.45 (s, 1H), 8.98 (d, J=2.9 Hz, 1H), 8.59 (dd, J=7.3, 2.1 Hz, 1H), 8.07 (br. s, 1H), 7.59 (br. s., 1H), 7.47-7.58 (m, 5H), 7.38-7.45 (m, 1H).
Preparation 4

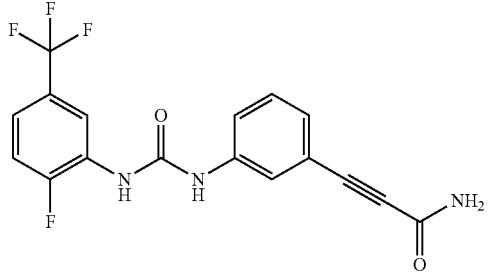 [SMILES: NC(=O)C#Cc1cccc(NC(=O)Nc2cc(C(F)(F)F)ccc2F)c1]

3-{3-[({[2-fluoro-5-(trifluoromethyl)phenyl]amino}carbonyl)amino]phenyl}prop-2-ynamide To a mixture of propynoic acid amide (41.4 mg, 0.60 mmol), 1-[2-fluoro-5-(trifluoromethyl)phenyl]-3-(3-iodophenyl)urea (169.7 mg, 0.40 mmol), triethylamine (0.167 mL, 1.2 mmol), dichlorobis(triphenylphosphine)palladium(II) (22.5 mg, 0.032 mmol), and triphenylphosphine (5.2 mg, 0.020 mmol) in 3.0 mL DMF (degassed) was added copper (I)iodide (7.6 mg, 0.04 mmol) and the reaction stirred at rt for 15 hours. The reaction was partitioned between EtOAc and H$_2$O/brine mixture. The EtOAc layer was washed 3 times with H$_2$O/brine mixture, then brine, dried with anhydrous Na$_2$SO$_4$ and rotary evaporated to a solid. The solid was triturated with hot MeOH and then triturated with hot EtOAc to give the title compound as a light tan solid (107.4 mg, 74%). $^1$H NMR (DSMO-d6) δ: 9.33 (s, 1H), 8.95 (d, J=2.1 Hz, 1H), 8.60 (dd, J=7.3, 2.1 Hz, 1H), 8.17 (br. s., 1H), 7.87 (s, 1H), 7.67 (br. s., 1H), 7.37-7.55 (m, 4H), 7.17-7.25 (m, 1H)

EXAMPLE 1

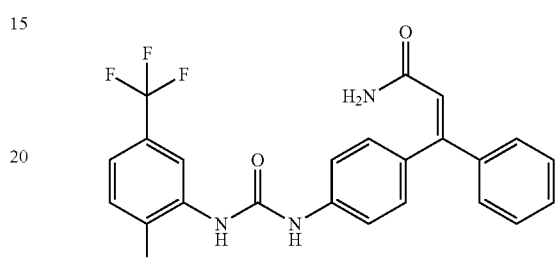

(2Z)-3-{4-[({[2-fluoro-5-(trifluoromethyl)phenyl]amino}carbonyl)amino]phenyl}-3-phenylacrylamide A mixture of 3-{4-[({[2-fluoro-5-(trifluoromethyl)phenyl]amino}carbonyl)amino]phenyl}prop-2-ynamide (31.0 mg, 0.085 mmol), iodobenzene (0.010 mL, 0.089 mmol), diethylamine (0.029 mL, 0.281 mmol), formic acid (0.0083 mL, 0.221 mmol), and bis(dibenzylideneacetone)palladium(0) (3.4 mg, 0.006 mmol) in 1.1 mL EtOAc (degassed) was heated at 75° C. After 2 hours, an additional 2 mg bis(dibenzylideneacetone)palladium(0) was added and the reaction continued for 18 hours. The reaction was partitioned between EtOAc and H$_2$O/brine mixture. The EtOAc layer was washed with dilute aqueous HCl, then aqueous Na$_2$CO$_3$, brine, dried with anhydrous Na$_2$SO$_4$ and rotary evaporated. The crude product was chromatographed eluting with EtOAc/CHCl$_3$ and the resulting solid again chromatographed with MeOH/CHCl$_3$ to give the title compound as an off-white solid (8.8 mg, 23%). $^1$H NMR (Acetone-d6) δ: 8.79 (dd, J=7.5, 2.2 Hz, 1H), 8.43 (d, J=2.9 Hz, 1H), 8.41 (s, 1H), 7.39-7.44 (m, 2H), 7.27-7.39 (m, 7H), 7.11-7.16 (m, 3H), 6.76 (br. s., 1H), 6.49 (s, 1H)

EXAMPLE 2

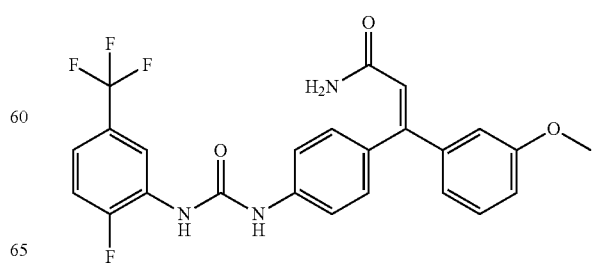

(2E)-3-{4-[({[2-fluoro-5-(trifluoromethyl)phenyl]amino}carbonyl)amino]phenyl}-3-(3-methoxyphenyl)acrylamide A mixture of 3-{4-[({[2-fluoro-5-(trifluoromethyl)phenyl]amino}carbonyl)amino]phenyl}prop-2-ynamide (31.0 mg, 0.085 mmol), 3-iodoanisole (0.010 mL, 0.089 mmol), diethylamine (0.029 mL, 0.281 mmol), formic acid (0.0083 mL, 0.221 mmol), and bis(dibenzylideneacetone)palladium(0) (3.4 mg, 0.006 mmol) in 1.4 mL EtOAc (degassed) was heated at 75° C. for 17 hours. The reaction was partitioned between EtOAc and H$_2$O/brine mixture. The EtOAc layer was washed with dilute aqueous HCl, then aqueous NaHCO$_3$, brine, and dried with anhydrous Na$_2$SO$_4$ to give 20 mL of EtOAc solution of crude material. The EtOAc solution was filtered past a plug of silica gel eluting with EtOAc, evaporated, and the resulting solid chromatographed eluting with CHCl$_3$/MeOH to give the title compound as a light tan solid (12.0 mg, 30%). $^1$H NMR (Acetone-d6) δ: 8.80 (d, J=5.9 Hz, 1H), 8.46 (s, 1H), 8.42 (d, J=2.6 Hz, 1H), 7.33-7.47 (m, 4H), 7.23-7.29 (m, 1H), 7.15 (d, J=8.5 Hz, 2H), 6.91-7.00 (m, 2H), 6.82-6.87 (m, 2H), 6.65 (br. s., 1H), 6.47 (s, 1H), 3.77 (s, 3H).

EXAMPLE 3

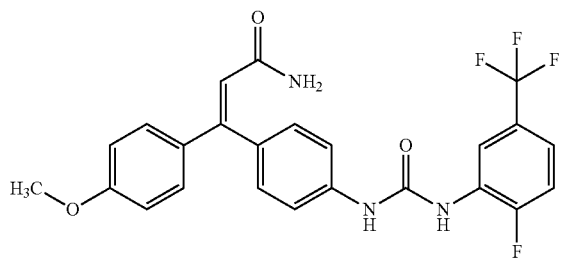 [SMILES: COc1ccc(/C(=C/C(N)=O)c2ccc(NC(=O)Nc3cc(C(F)(F)F)ccc3F)cc2)cc1]

(2E)-3-{4-[({[2-fluoro-5-(trifluoromethyl)phenyl]amino}carbonyl)amino]phenyl}-3-(4-methoxyphenyl)acrylamide A mixture of 3-{4-[({[2-fluoro-5-(trifluoromethyl)phenyl]amino}carbonyl)amino]phenyl}prop-2-ynamide (31.0 mg, 0.085 mmol), 4-iodoanisole (0.010 mL, 0.089 mmol), diethylamine (0.029 mL, 0.281 mmol), formic acid (0.0083 mL, 0.221 mmol), and bis(dibenzylideneacetone)palladium(0) (3.4 mg, 0.006 mmol) in 1.4 mL EtOAc (degassed) was heated at 75° C. for 20 hours. The reaction was partitioned between EtOAc and H$_2$O/brine mixture. The EtOAc layer was washed with dilute aqueous HCl, then aqueous NaHCO$_3$, brine, and dried with anhydrous Na$_2$SO$_4$ to give 20 mL of EtOAc solution of crude material. The EtOAc solution was filtered past a plug of silica gel eluting with EtOAc, evaporated, and the resulting solid chromatographed eluting with EtOAc/CHCl$_3$ to give the title compound as a grey-purple solid (12.5 mg, 31%). $^1$H NMR (Acetone-d6) δ: 8.80 (d, J=7.6 Hz, 1H), 8.42 (s, 2H), 7.32-7.45 (m, 4H), 7.21-7.26 (m, 2H), 7.10-7.16 (m, 2H), 6.98 (br. s., 1H), 6.88-6.94 (m, 2H), 6.63 (br. s., 1H), 6.43 (s, 1H), 3.81 (s, 3H).

EXAMPLE 4

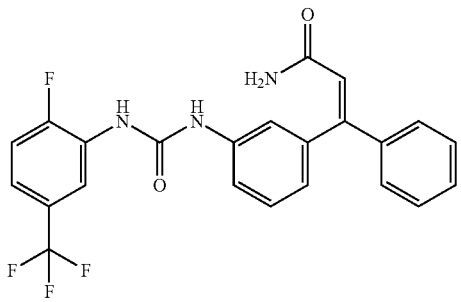 [SMILES: NC(=O)/C=C(/c1ccccc1)c1cccc(NC(=O)Nc2cc(C(F)(F)F)ccc2F)c1]

(2Z)-3-{3-[({[2-fluoro-5-(trifluoromethyl)phenyl]amino}carbonyl)amino]phenyl}-3-phenylacrylamide A mixture of 3-{3-[({[2-fluoro-5-(trifluoromethyl)phenyl]amino}carbonyl)amino]phenyl}prop-2-ynamide (31.0 mg, 0.085 mmol), iodobenzene (0.010 mL, 0.089 mmol), diethylamine (0.029 mL, 0.281 mmol), formic acid (0.0083 mL, 0.221 mmol), and bis(dibenzylideneacetone)palladium(0) (3.4 mg, 0.006 mmol) in 1.1 mL EtOAc (degassed) was heated at 75° C. for 16 hours. The reaction was partitioned between EtOAc and H$_2$O/brine mixture. The EtOAc layer was washed with H$_2$O/brine mixture, brine, dried with anhydrous Na$_2$SO$_4$ and rotary evaporated. The crude material was chromatographed eluting with EtOAc/CHCl$_3$ to give the higher R$_f$ material as an off-white solid. The solid was recrystallized from EtOAc/hexane to give the title compound as a white solid (7.5 mg, 20%). $^1$H NMR (CD3CN) δ: 8.54-8.58 (m, 1H), 7.89 (s, 1H), 7.71 (d, J=3.2 Hz, 1H), 7.14-7.39 (m, 10H), 6.78-6.82 (m, 1H), 6.39 (s, 1H), 6.14 (br. s, 1H), 5.79 (br. s, 1H).

EXAMPLE 5

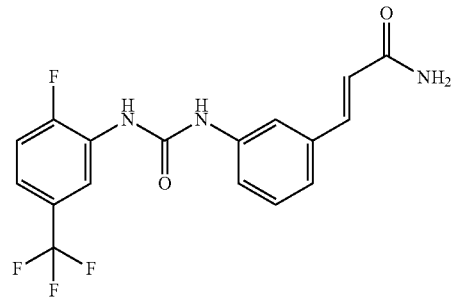

(2E)-3-{3-[({[2-fluoro-5-(trifluoromethyl)phenyl]amino}carbonyl)amino]phenyl}acrylamide The lower R$_f$ eluting material from the chromatography of the crude reaction mixture from Example 4 was obtained as an off-white solid and then recrystallized from EtOAc/hexane to give the title compound as a white solid (8.2 mg). $^1$H NMR (CD3CN) δ: 8.55-8.60 (m, 1H), 7.84 (s, 1H), 7.61-7.64 (m, 2H), 7.45-7.50 (m, 1H), 7.28-7.34 (m, 2H), 7.24 (t, J=7.8 Hz, 1H), 7.12-7.17 (m, 1H), 6.74 (d, J=12.6 Hz, 1H), 6.31 (br. s, 1H), 6.03 (d, J=12.6 Hz, 1H), 5.91 (br. s., 1H).

EXAMPLE 6

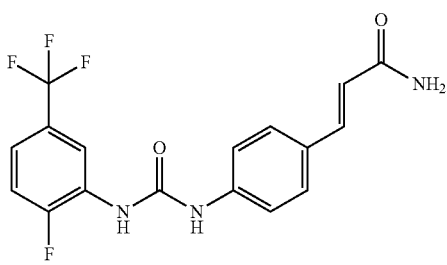

(2E)-3-{4-[({[2-fluoro-5-(trifluoromethyl)phenyl]amino}carbonyl)amino]phenyl}acrylamide A mixture of acrylamide (6.2 mg, 0.087 mmol), 1-[2-fluoro-5-(trifluoromethyl)phenyl]-3-(4-iodophenyl)urea (9.2 mg, 0.022 mmol), and palladium(II) acetate (1.9 mg, 0.0087 mmol) in 0.6 mL degassed DMF:triethylamine (1:1) was reacted at 90° C. After 2.5 hours, the heating was stopped and the reaction stored at rt for 3 days in the dark. Then a catalytic amount of palladium(II) acetate was added and the heating resumed at 90° C. for 7.5 hours, then the temperature lowered to 65° C. for 16 hours. The reaction was partitioned between EtOAc and $H_2O$/brine mixture. The EtOAc layer was washed with dilute aqueous HCl, then aqueous $NaHCO_3$, brine, dried with anhydrous $Na_2SO_4$ and evaporated. The resulting solid was chromatographed eluting with $CHCl_3$/MeOH and then triturated with a $CHCl_3$ plus 40% EtOAc/hexane mixture to give the title compound as a light tan solid (3.9 mg, 49%). $^1$H NMR (Acetone-d6) δ: 8.76-8.83 (m, 2H), 8.40 (d, J=2.6 Hz, 1H), 7.58-7.63 (m, 2H), 7.37-7.57 (m, 5H), 6.91 (br. s, 1H), 6.63 (d, J=15.8 Hz, 1H), 6.32 (br. s, 1H)

EXAMPLE 7

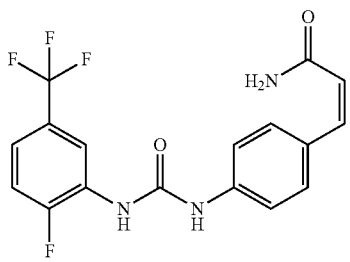 [SMILES: NC(=O)/C=C\c1ccc(NC(=O)Nc2cc(C(F)(F)F)ccc2F)cc1]

(2Z)-3-{4-[({[2-fluoro-5-(trifluoromethyl)phenyl]amino}carbonyl)amino]phenyl}acrylamide A mixture of 3-{4-[({[2-fluoro-5-(trifluoromethyl)phenyl]amino}carbonyl)amino]phenyl}prop-2-ynamide (12.2 mg, 0.033 mmol), 0.005 mL quinoline, and 4 mg Lindlar catalyst in 1.5 mL EtOAc was reacted under a balloon of hydrogen. After 1.75 hours, an additional catalytic amount of Lindlar catalyst was added and the reaction continued for an additional 1 hour. The reaction mixture was partitioned between EtOAc and dilute aqueous HCl, the EtOAc layer washed with $H_2O$, brine, dried with $Na_2SO_4$ and evaporated. The crude material was chromatographed eluting with hexane/acetone to give the title compound as a white solid (10.3 mg, 84%). $^1$H NMR (Acetone-d6) δ: 8.79 (d, J=7.9 Hz, 1H), 8.69 (br. s., 1H), 8.37 (br. s., 1H), 7.75 (d, J=8.5 Hz, 2H), 7.50 (d, J=8.8 Hz, 2H), 7.35-7.43 (m, 2H), 6.93 (br. s., 1H), 6.64 (d, J=12.9 Hz, 1H), 6.41 (br. s., 1H), 5.97 (d, J=12.9 Hz, 1H)

EXAMPLE 8

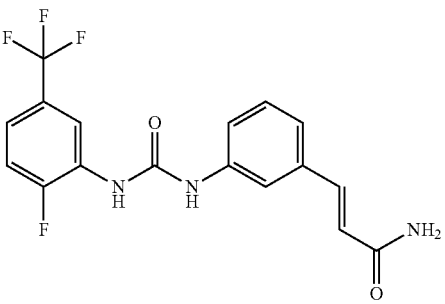 [SMILES: NC(=O)/C=C/c1cccc(NC(=O)Nc2cc(C(F)(F)F)ccc2F)c1]

(2E)-3-{3-[({[2-fluoro-5-(trifluoromethyl)phenyl]amino}carbonyl)amino]phenyl}acrylamide A mixture of acrylamide (24.7 mg, 0.347 mmol), 1-[2-fluoro-5-(trifluoromethyl)phenyl]-3-(3-iodophenyl)urea (36.8 mg, 0.087 mmol), and palladium(II) acetate (7.8 mg, 0.035 mmol) in 0.8 mL degassed DMF:triethylamine (1:1) was reacted at 75° C. After 14.5 hours a catalytic amount of palladium(II) acetate was added, the temperature increased to 85° C., and the reaction continued for an additional 3.5 hours. The reaction was partitioned between EtOAc and $H_2O$/brine mixture. The EtOAc layer was washed with dilute aqueous HCl, then aqueous $NaHCO_3$, brine, dried with anhydrous $Na_2SO_4$ and evaporated. The resulting solid was triturated with $CHCl_3$/MeOH to give the title compound as a light tan solid (8.2 mg, 26%). $^1$H NMR (Acetone-d6) δ: 8.73-8.82 (m, 2H), 8.41 (br. s., 1H), 7.94 (s, 1H), 7.53 (d, J=15.7 Hz, 1H), 7.30-7.48 (m, 4H), 7.21-7.27 (m, 1H), 7.10 (br. s., 1H), 6.70 (d, J=15.7 Hz, 1H), 6.41 (br. s., 1H).

The present invention is not to be limited in scope by the exemplified embodiments which are intended as illustrations of single aspects of the invention only. Indeed, various modifications of the invention in addition to those described herein will become apparent to those skilled in the art from the foregoing description. For example, the novel compounds of this invention include any compound which is a (2E) or (2Z)-3-{4-[({[aryl]amino}carbonyl)amino]phenyl}-3-acrylamide or phenylacrylamide or lower alkyl acrylamide or phenylacrylamide and, in particular, a (2E) or (2Z)-3-{4-[({[halo-substituted and/or halo lower alkyl-substituted aryl]amino}carbonyl)amino]phenyl}-3-acrylamide or phenylacrylamide or lower alkyl acrylamide or phenylacrylamide and binds to a tyrosine kinase receptor, e.g. a VEGF and/or PDGF receptor.

These compounds may be prepared and tested for tyrosine kinase inhibiting activity by the preparatory methods and assays disclosed above.

Such modifications are intended to fall within the scope of the appended claims.

All references cited herein are hereby incorporated by reference in their entirety for all purposes. Also, the compounds of the present invention may be tested by the various in-vitro and in-vivo assays disclosed in such references to demonstrate the claimed utilities.

We claim:

1. A compound of formula I:

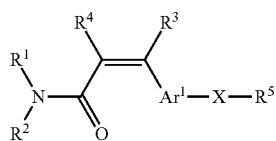

or a pharmaceutically acceptable salt thereof; wherein:
$R^1$ is selected from the group consisting of hydrogen and lower alkyl;
$R^2$ is selected from the group consisting of hydrogen and lower alkyl;
$R^3$ is selected from the group consisting of hydrogen, alkyl, phenyl and substituted phenyl;
$R^4$ is selected from the group consisting of hydrogen and $C_1$ to $C_8$ alkyl;
$Ar^1$ is phenyl;
X is

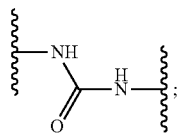

$R^5$ is selected from the group consisting of phenyl and substituted phenyl.

2. The compound of claim 1, wherein $R^1$ and $R^2$ are hydrogen.

3. The compound of claim 1, wherein $R^3$ is selected from the group consisting of hydrogen, phenyl and alkyloxyphenyl.

4. The compound of claim 1, wherein $R^4$ is hydrogen.

5. The compound of claim 1, wherein $Ar^1$ is phenyl.

6. The compound of claim 1, wherein, X is -HN—C(O)—NH—.

7. The compound of claim 1, wherein, $R^5$ is selected from the group consisting of phenyl and halo-substituted and halo lower alkyl-substituted phenyl.

8. The compound of claim 1, wherein $R^5$ is a fluoro, trifluoromethylphenyl.

9. The compound of claim 1 selected from the group consisting of:
(2Z)-3-{4-[({[2-fluoro-5-(trifluoromethyl)phenyl]amino}carbonyl)amino]phenyl}-3-phenylacrylamide;
(2E)-3-{4-[({[2-fluoro-5-(trifluoromethyl)phenyl]amino}carbonyl)amino]phenyl}-3-(3-methoxyphenyl)acrylamide;
(2E)-3-{4-[({[2-fluoro-5-(trifluoromethyl)phenyl]amino}carbonyl)amino]phenyl}-3-(4-methoxyphenyl)acrylamide;
(2Z)-3-{3-[({[2-fluoro-5-(trifluoromethyl)phenyl]amino}carbonyl)amino]phenyl}-3-phenylacrylamide;
(2E)-3-{3-[({[2-fluoro-5-(trifluoromethyl)phenyl]amino}carbonyl)amino]phenyl}acrylamide;
(2E)-3-{4-[({[2-fluoro-5-(trifluoromethyl)phenyl]amino}carbonyl)amino]phenyl}acrylamide;
(2Z)-3-{4-[({[2-fluoro-5-(trifluoromethyl)phenyl]amino1 carbonyl)amino]phenyl}acrylamide; and
(2E)-3-{3-[({[2-fluoro-5-(trifluoromethyl)phenyl]amino}carbonyl)amino]phenyl}acrylamide;
or a pharmaceutically acceptable salt thereof.

10. The compound of claim 1 selected from the group consisting of:
(2Z)-3-{4-[({[2-fluoro-5-(trifluoromethyl)phenyl]amino}carbonyl)amino]phenyl}-3-phenylacrylamide;
(2E)-3-{4-[({[2-fluoro-5-(trifluoromethyl)phenyl]amino}carbonyl)amino]phenyl}-3-(3-methoxyphenyl)acrylamide;
(2E)-3-{4-[({[2-fluoro-5-(trifluoromethyl)phenyl]amino}carbonyl)amino]phenyl}-3-(4-methoxyphenyl)acrylamide; and
(2Z)-3-{4-[({[2-fluoro-5-(trifluoromethyl)phenyl]amino}carbonyl)amino]phenyl}acrylamide;
or a pharmaceutically acceptable salt thereof.

11. The compound of claim 1 selected from the group consisting of:
(2Z)-3-{4-[({[2-fluoro-5-(trifluoromethyl)phenyl]amino}carbonyl)amino]phenyl}-3-phenylacrylamide;
(2E)-3-{4-[({[2-fluoro-5-(trifluoromethyl)phenyl]amino}carbonyl)amino]phenyl}-3-(3-methoxyphenyl)acrylamide; and
(2E)-3-{4-[({[2-fluoro-5-(trifluoromethyl)phenyl]amino}carbonyl)amino]phenyl}-3-(4-methoxyphenyl)acrylamide;
or a pharmaceutically acceptable salt thereof.

12. The compound of claim 1 that is (2E)-3-{4-[({[2-fluoro-5-(trifluoromethyl)phenyl]amino}carbonyl)amino]phenyl}-3-(4-methoxyphenyl)acrylamide; or a pharmaceutically acceptable salt thereof.

13. A compound that is a (2E) or (2Z)-3-{4-[({[phenyl]amino}carbonyl)amino]phenyl}-3-acrylamide or phenylacrylamide, or lower alkyl acrylamide or phenylacrylamide; or a pharmaceutically acceptable salt thereof, and binds to a VEGF and/or a PDGF receptor.

14. A compound according to claim 13 that is a (2E) or (2Z)-3-{4-[({[halo-substituted and/or halo lower alkyl-substituted phenyl]amino}carbonyl)amino]phenyl}-3-acrylamide, or phenylacrylamide or lower alkyl acrylamide; or a pharmaceutically acceptable salt thereof.

15. A pharmaceutical composition comprising at least one compound of claim 1 or a pharmaceutically acceptable salt thereof, and a pharmaceutically acceptable carrier or excipient.

* * * * *